US008715202B2

(12) United States Patent
Cardoso et al.

(10) Patent No.: US 8,715,202 B2
(45) Date of Patent: May 6, 2014

(54) MINIMALLY INVASIVE IMAGE-BASED DETERMINATION OF CARBON DIOXIDE ($CO_2$) CONCENTRATION IN EXHALED BREATH

(75) Inventors: George Cunha Cardoso, Webster, NY (US); Lalit Keshav Mestha, Fairport, NY (US); Beilei Xu, Penfield, NY (US)

(73) Assignee: Xerox Corporation, Norwalk, CT (US)

( * ) Notice: Subject to any disclaimer, the term of this patent is extended or adjusted under 35 U.S.C. 154(b) by 261 days.

(21) Appl. No.: 13/246,560

(22) Filed: Sep. 27, 2011

(65) Prior Publication Data
US 2013/0079658 A1    Mar. 28, 2013

(51) Int. Cl.
*A61B 5/08* (2006.01)
*G01J 1/22* (2006.01)

(52) U.S. Cl.
USPC ....... 600/532; 600/473; 600/529; 250/339.13

(58) Field of Classification Search
USPC ............. 600/529–543, 473–475; 250/339.12, 250/339.13
See application file for complete search history.

(56) References Cited

U.S. PATENT DOCUMENTS

| | | | | |
|---|---|---|---|---|
| 4,928,703 | A | * | 5/1990 | Wong ............................ 600/532 |
| 4,955,946 | A | * | 9/1990 | Mount et al. .................. 600/532 |
| 2003/0025081 | A1 | * | 2/2003 | Edner et al. ............... 250/339.09 |
| 2004/0111014 | A1 | * | 6/2004 | Hickle ........................... 600/300 |
| 2013/0181836 | A1 | * | 7/2013 | Cardoso et al. ............... 340/540 |

OTHER PUBLICATIONS

Fei et al. "Imaging Breathing Rate in the CO2 Absorption Band." Proceedings of the 2005 IEEE Engineering in Medicine and Biology 27th Annual Conference. Shanghai, China, Sep. 1-4, 2005, pp. 700-705.*
Vollmer et al. "IR Imaging of Gases: Quantitative Analysis." Inframation 2009 Proceedings, vol. 10, pp. 99-112.*
Jaffe, Michael B. "Infrared Measurement of Carbon Dioxide in the Human Breath: Breathe-Through" Devices from Tyndall to the Present Day. Anesth Analg. Sep. 2008;107(3):890-904.*
Vollmer et al. "IR Imaging of Gases: Potential Applications for CO2 Cameras." Inframation 2009 Proceedings, vol. 10, pp. 113-124.*
Fei et al. "Analysis of Breathing Air Flow Patterns in Thermal Imaging." Proceedings of the 28th IEEE EMBS Annual International Conference. New York City, USA, Aug. 30-Sep. 3, 2006, pp. 946-952.*

(Continued)

*Primary Examiner* — Navin Natnithithadha
*Assistant Examiner* — Meredith Weare
(74) *Attorney, Agent, or Firm* — Philip E. Blair; Fleit Gibbons Gutman Bongini & Bianco P.L.

(57) ABSTRACT

What is disclosed is a system and method for image-based determination of carbon dioxide ($CO_2$) concentration in exhaled breath. In one embodiment, an image of the exhaled airstream of a subject of interest is received. The image is captured using a mid-wave infrared camera system having an optical filter tuned to the infrared absorption band of $CO_2$. The image is preprocessed to isolate a region of pixels containing the exhaled airstream and intensity values of pixels in the identified region are normalized by a value of a known radiance such as that of the subject's nose or face. The image is analyzed to determine $CO_2$ concentration levels of the exhaled airstream using a calibration curve which relates pixel intensity to $CO_2$ concentrations. The calibration curve is derived using a physics-based parameterized model. The $CO_2$ concentration levels are determined and communicated to a computer workstation. Various embodiments are disclosed.

21 Claims, 16 Drawing Sheets

(56) References Cited

OTHER PUBLICATIONS

Murthy et al. "Touchless Monitoring of Breathing Function." Proceedings of the 26th Annual International Conference of the IEEE EMBS. San Francisco, CA, USA, Sep. 1-5, 2004, pp. 1196-1199.*

Xu et al., "Monitoring Respiration With A Thermal Imaging System", U.S. Appl. No. 13/103,406, filed May 9, 2011.

Wang et al., "Determining A Total Number Of People In An IR Image Obtained Via An IR Imaging System", U.S. Appl. No. 12/967,775, filed Dec. 14, 2010.

Al-Khalidi et al., "Tracking Human Face Features In Thermal Images for Respiration Monitoring", IEEE/ACS Int'l Conf. on Computer Systems and Applications (AICCSA), Hammamet, Tunisia, (2010).

* cited by examiner

MINIMALLY INVASIVE IMAGE-BASED DETERMINATION OF CARBON DIOXIDE ($CO_2$) CONCENTRATION IN EXHALED BREATH

TECHNICAL FIELD

The present invention is directed to systems and methods for an image-based monitoring of a patient's respiratory function such that a concentration of carbon dioxide ($CO_2$) in their exhaled breath as well as their respiration rate can be determined in a non-contact, minimally invasive monitoring environment.

BACKGROUND

Methods for monitoring the respiratory function of a person have many applications in medicine, sleep studies, polygraph testing, to name a few. Such systems use wires and electrodes or other physically invasive apparatus which contact the subject and thus may interfere with their convalescence. One important respiratory function desired to be monitored is the concentration of $CO_2$. $CO_2$ deficiency can trigger or exacerbate complaints such as: shortness of breath, chest pain, feelings of suffocation, numbness, irregular heartbeat, to name a few, including fatigue, weakness, exhaustion, nausea, and light-headedness. An assessment of $CO_2$ concentration and respiration rate helps the medical professional better diagnose whether the person is suffering from hyperventilation (overbreathing or hypocapnea) or hypoventilation (underbreathing or hypercapnea). One problem with breathing assessment is that once a patient becomes aware he/she is having their respiration monitored, they tend to unconsciously change their normal breathing pattern. This sometimes makes it difficult to get reliable assessments of a patient's breathing function. An inconspicuous measurement system is highly desirable which can facilitate the assessment of a patient's respiratory function without their participation or even knowledge.

Accordingly, what is needed in this art are increasingly sophisticated methods for assessing a patient's respiratory function in a minimally invasive, non-contact respiration monitoring environment.

INCORPORATED REFERENCES

The following U.S. patents, U.S. patent applications, and Publications are incorporated herein in their entirety by reference.

"Monitoring Respiration With A Thermal Imaging System", U.S. patent application Ser. No. 13/130,406, by Xu et al.

"Determining A Total Number Of People In An IR Image Obtained Via An IR Imaging System", U.S. patent application Ser. No. 12/967,775 by Wang et al.

"*Tracking Human Face Features In Thermal Images For Respiration Monitoring*", F. Q. Al-Khalidi, R. Saatchi, D. Burke, H. Elphick, IEEE/ACS Int'l Conf. on Computer Systems and Applications (AICCSA), Hammamet, Tunisia, (2010).

"*Principles of Anatomy and Physiology*", Gerard J. Tortora, Bryan H. Derrickson, Wiley; $13^{th}$ Ed. (2011), ISBN-13: 978-0470565100.

"*Infrared Thermal Imaging: Fundamentals, Research and Applications*", Michael Vollmer, Klaus Peter Möllmann, Wiley-VCH; $1^{st}$ Ed. (2010) ISBN-13: 978-3527407170.

"*Capnography*", J. S. Gravenstein (Editor), Michael B. Jaffe (Editor), Nikolaus Gravenstein (Editor), David A. Paulus (Editor), Cambridge University Press; $2^{nd}$ Ed. (2011), ISBN-13: 978-0521514781.

"*Respiratory Physiology: The Essentials*", John B. West, Lippincott Williams & Wilkins; $9^{th}$ Ed. (2011), ISBN-13: 978-1609136406.

"*Oxygen Transport in Biological Systems: Modeling of Pathways from Environment to Cell*", S. Egginton (Editor), H. F. Ross (Editor), Cambridge University Press; $1^{st}$ Ed. (1993), ISBN-13: 978-0521414883.

BRIEF SUMMARY

What is disclosed is a novel system and method for determining the concentration of carbon dioxide in an image of exhaled breath and for determining the patient's respiration rate. The present system and method utilizes a mid-wave infrared camera to capture images of a patient's exhalation airstream utilizing a narrow band-pass filter set at an IR absorption wavelength of $CO_2$. As more fully disclosed herein, an algorithm and calibration method are provided. The teachings hereof effectuate an assessment of a patient's respiratory function in a non-contact and minimally invasive manner.

In one example embodiment, the present method for image-based determination of carbon dioxide ($CO_2$) concentration in exhaled breath involves the following. First, an image of the exhaled airstream of a subject of interest is received. The image is captured using a mid-wave infrared camera system having at least one optical filter tuned to the infrared absorption band of $CO_2$. This optical filter is a narrow band-pass filter which increases a contrast of $CO_2$ relative to the emissions of background blackbodies. Each of the received images comprises, at least in part, an array of pixels having respective intensity values obtained at desired absorption bands of $CO_2$. The image is preprocessed to isolate a region of pixels containing the exhaled airstream and intensity values of pixels in the identified region are normalized by a value of a known radiance such as that of the subject's nose or face. In a manner more fully disclosed herein, the image is analyzed to determine $CO_2$ concentration levels of the exhaled airstream using a calibration curve which relates pixel intensity values to $CO_{22}$ concentrations. The calibration curve is derived using a physics-based parameterized model which relates pixel intensity to $CO_2$ concentration in mmHg units. The $CO_2$ concentration levels are determined and communicated to a memory, a storage device, a graphical display, and/or a computer workstation.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for determining the concentration of carbon dioxide in an image of exhaled breath in a minimally invasive and non-contact manner utilizing a mid-wave infrared (MWIR) video camera system to capture video images of the exhalation stream exiting the subject's nose and mouth Non-Limiting Definitions A "subject of interest", as used herein, refers to a human for which respiratory function is intended to be monitored for respiratory function assessment according to the teachings hereof. Although the term "human", "person", or "patient" may be used throughout this text, the subject of interest intended to be monitored for respiratory function may be something other than a human such as, an animal, reptile, or even insects and plants. Therefore, the explanatory use of the terms "person" or "patient" are not to be viewed as limiting the scope of the appended claims to human beings.

Figure 1:
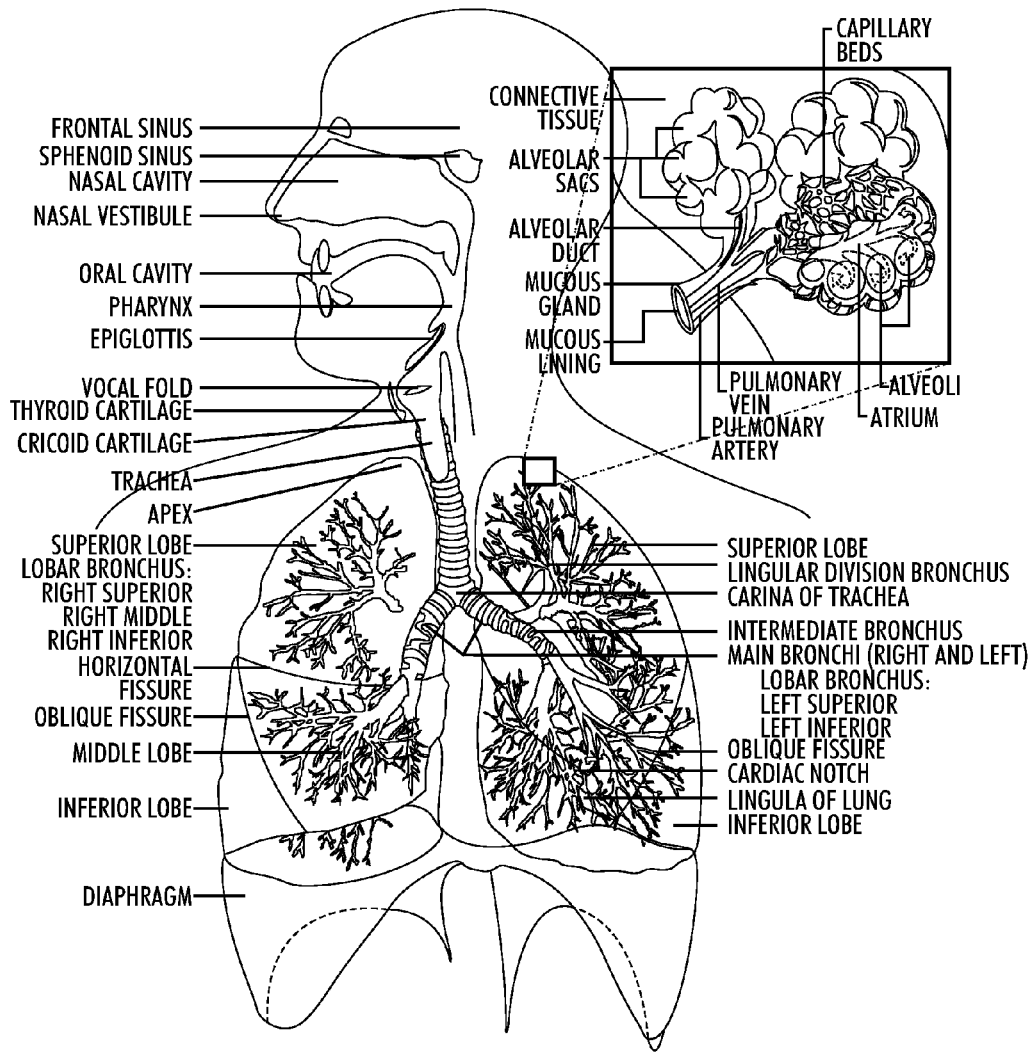
FIG. 1 is a medical diagram showing the respiratory system of a human.

The "respiratory system" is the anatomical portion of an organism that introduces respiratory gases into the interior of the organism, performs gas exchange, and expels waste gases back out into the surrounding environment. In mammals, the anatomical features of their respiratory system include airways, lungs, and respiratory muscles. FIG. 1 is a diagram showing the respiratory system of a human. Other species, such as insects, reptiles, and amphibians have respiratory systems with simple anatomical features. In some, their skin plays a role in respiration. Plants also have respiratory systems which include anatomical features such as holes on the undersides of leaves known as stomata, but the directionality of gas exchange tends to be opposite to that in animals. During respiration, molecules of oxygen and carbon dioxide are passively exchanged, by diffusion, between the gaseous external environment and the organism. In humans, carbon dioxide is one of the mediators of auto-regulation of blood supply, i.e., if $CO_2$ levels are high, capillaries around tissue expand to allow a greater blood flow to that tissue. The respiratory centers seek to maintain an arterial $CO_2$ pressure of 40 mmHg. Although the body requires oxygen for metabolism, low oxygen levels normally do not stimulate breathing. Rather, breathing is stimulated by high concentrations of carbon dioxide. As a result, breathing low-pressure air or a gas mixture with no oxygen at all (such as pure nitrogen) can lead to loss of consciousness without ever experiencing air hunger because the body does not detect high concentrations of carbon dioxide. With hyperventilation, the $CO_2$ content of arterial blood may be lowered to 10-20 mmHg, and the respiratory drive is diminished. This is why one can hold their breath longer after hyperventilating than without hyperventilating but this carries the risk of unconsciousness resulting before the person feels the need to breathe again; which is why hyperventilation is particularly dangerous before free diving.

A "respiration function" consists of: inhalation, gas exchange, and exhalation. Inhalation is initiated by the movement of a diaphragmatic muscle and supported intercostal muscles. Under normal conditions, the diaphragm is the primary driver of inhalation. When the diaphragm contracts, the ribcage expands and the contents of the abdomen are moved downward. This results in a larger thoracic volume and negative pressure (with respect to atmospheric pressure) inside the thorax. As the pressure in the chest falls, air moves into the conducting zone where the incoming air is warmed, and humidified. Gas exchange is a primary function of the respiratory system. Molecules of gases are exchanged between the external environment and an organism's system. This exchange facilitates oxygenation of the blood and a removal of carbon dioxide and other metabolic wastes from the blood. As gas exchange occurs, the acid-base balance of the body is maintained. The cellular mechanism of gas exchange is carried out by the simple phenomenon of pressure difference. When the atmospheric pressure is low outside, then air from the lungs flow out into the environment. When the air pressure is low inside the lungs, the opposite occurs. Exhalation is generally a passive process due to the natural elasticity of lung tissue which causes them to recoil from the stretch of inhalation thus forcing air out until the pressures in the chest and the pressure of the outside atmosphere reach equilibrium. During forced exhalation, as when blowing out a candle, expiratory muscles including abdominal muscles and internal intercostal muscles, generate abdominal and thoracic pressure which forces air out of the lungs. During forced inhalation, as when taking a deep breath, external intercostal muscles and accessory muscles aid in expanding the thoracic cavity. During vigorous inhalation (at rates exceeding 35 breaths per minute), or in an approaching respiratory failure, accessory muscles such as the sternocleidomastoid, platysma, the scalene muscles of the neck as well as the pectoral muscles and latissimus dorsi of respiration are recruited for support.

A "respiration rate" is the number of breaths a subject takes in a certain amount of time (typically in breaths per minute). Normal respiratory exhalation produces approximately 2.3 pounds (1 kg) of carbon dioxide per day per person. During physical exertion when the body requires oxygenation at an increased rate, the respiration rate increases. Respiration rates may increase without physical activity due to fever, for example, or other medical conditions.

Figure 2:
FIG. 2 is an IR image captured of a subject's profile to illustrate the exhalation airstream exiting the subject's nose.
Figure 3:
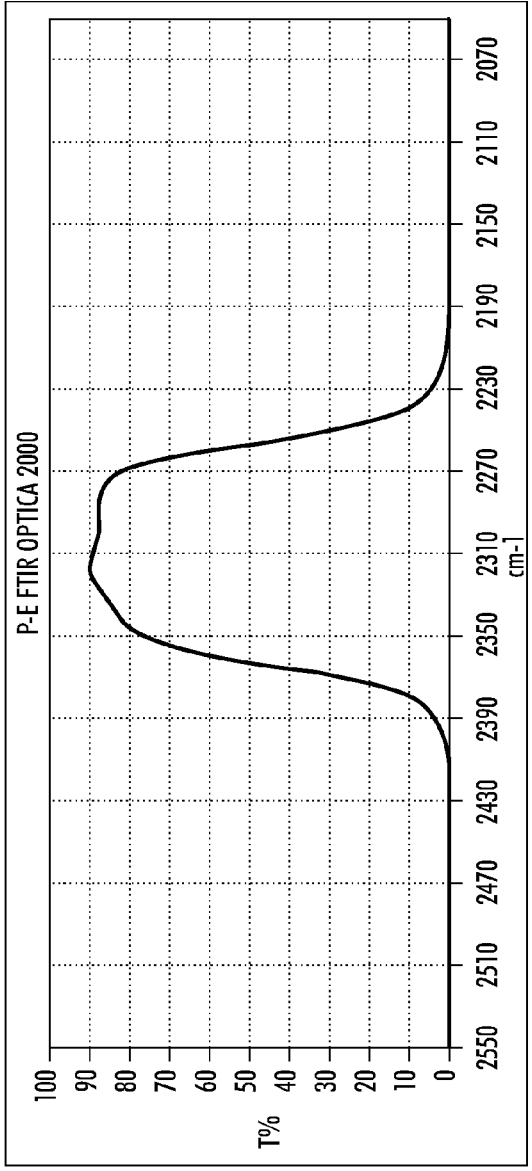
FIG. 3 shows the specifications of the $CO_2$ band-pass filter used to capture the IR image of FIG. 2.

An "IR Image" is an infrared image of a subject of interest obtained using an IR camera. A fully-populated IR image consists of pixels each having an intensity value at a desired spectral band. IR images are captured in the mid-wave region of the infrared spectrum (approximately 3 to 8 μm), also called the intermediate infrared (IIR) region, using a mid-wave infrared camera aimed at an extremity of the subject's head and face such that their exhalation airstream can be captured in the image and processed in accordance with the teachings hereof. An example IR image capturing a subject of interest's exhaled breath is shown in FIG. 2. The image of FIG. 2 was captured using an off-the-shelf optical band-pass filter designed for the emissivity of $CO_2$ radiance. FIG. 3 lists the specification of a Spectrogon $CO_2$ band-pass filter available in commerce.

A "mid-wave infrared (MWIR) camera" is an imaging system capable of capturing an IR image. Such cameras are available for purchase in various streams of commerce. Vendors include Xenics and FLIR. Many MWIR video cameras offer high thermal sensitivity, short integration times, and high spatial resolution. Some cameras incorporate a high sensitivity 640×512 format HgCdTe infrared detector integrated into a sealed housing enabling a range of diverse applications involving high resolution tracking, radiometric data collection, and high speed imaging, to name a few. The infrared camera system and filters used herein are designed to collect the light emitted by the roto-vibrational radiation from $CO_2$ molecules. Since carbon dioxide absorbs strongly between 4.1 and 4.4 μm this is a band of interest. The IR camera includes a spectral band-pass filter to increase the contrast of the $CO_2$ emissions relative to the background blackbody emissions. Since we are detecting $CO_2$ radiance from roto-vibrational emission, an illumination source is not necessary. As such, image can be obtained in a completely dark and cold room.

"Pre-processing the images" means isolating the location of the exhaled airstream in the image. One method which identifies facial features associated with a respiratory function is disclosed in the above-incorporated reference "*Monitoring Respiration With A Thermal Imaging System*", by Xu et al.

A "facial feature associated with respiration" refers to an air passageway through which the subject's respiratory system receives oxygenated air into the lungs during inhalation and expels $CO_2$ rich air out of the lungs during exhalation. In humans, the facial features associated with respiration are the nose and mouth.

Figure 4:
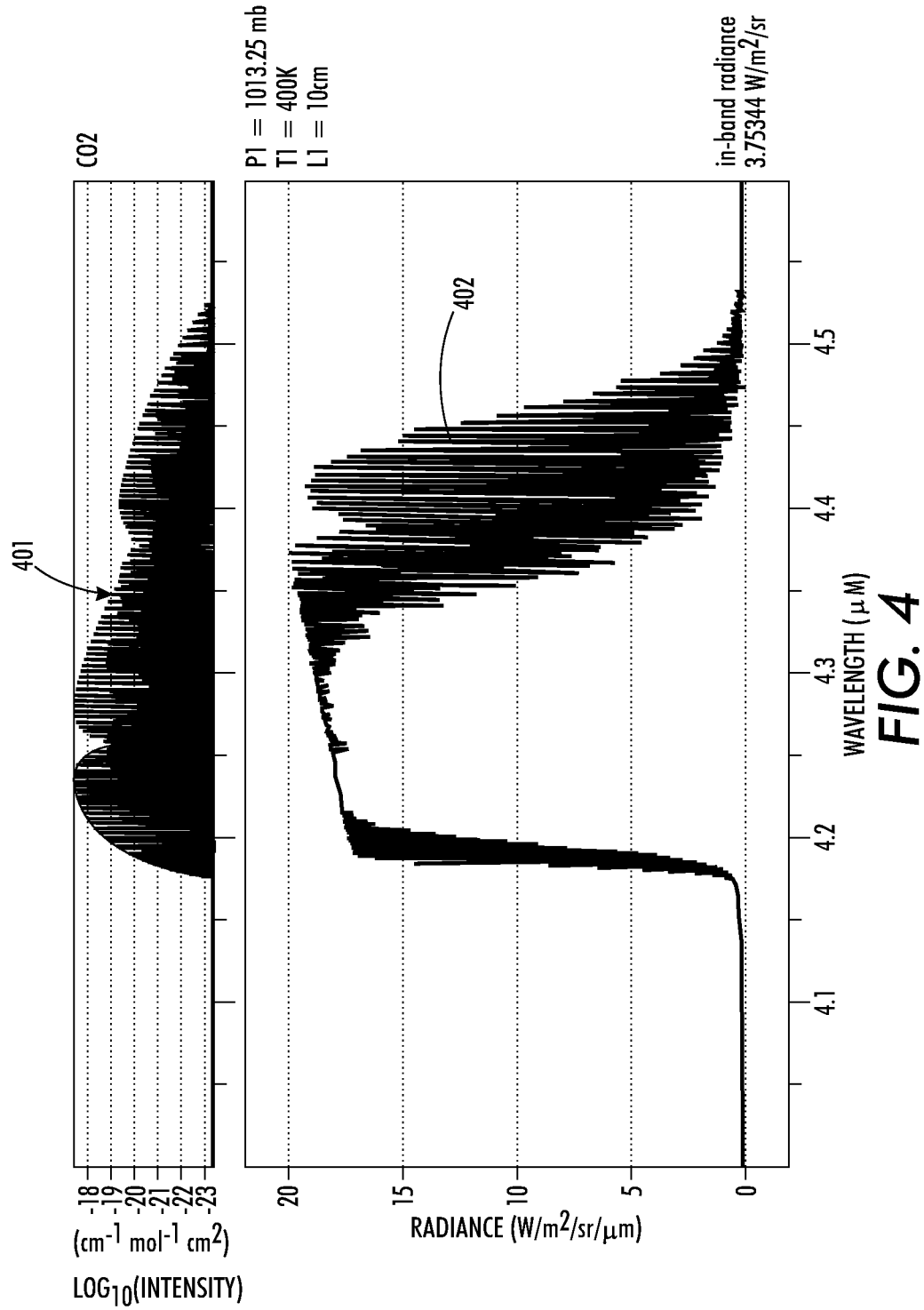
FIG. 4 shows the IR spectrum of $CO_2$ (4.0 kPa total pressure)

"Carbon dioxide" (chemical formula $CO_2$ also written as simply CO2) is a compound composed of two oxygen atoms covalently bonded to a carbon atom. Carbon dioxide is a naturally occurring gas that exists in the Earth's atmosphere at a concentration of approximately 0.039% by unit volume at standard temperature and pressure. $CO_2$ is toxic in high concentrations. A 1% concentration (10,000 ppm) will make people feel drowsy, fatigued, and ill. Concentrations of 7% to 10% cause dizziness, headache, visual and hearing dysfunction, and unconsciousness within minutes depending on the degree of exposure. $CO_2$ absorbs strongly in the infrared. The IR spectrum of $CO_2$ (4.0 kPa total pressure) is shown in FIG. 4. Carbon dioxide ($CO_2$) absorption lines (top plot at 401) and radiance spectrum (bottom plot at 402) for Pressure=1 atm, Temp=400° K, distance L=10 cm, and VMR=0.1. VMR is the volume mixing ratio. A VMR=0.1 is equivalent to 10% molecules of the gas of interest and the remaining molecules of a gas that is optically inert for purposes of the calculation Because the IR spectrum of each molecule is unique, it can serve as a signature or fingerprint to identify the molecule.

Figure 5:
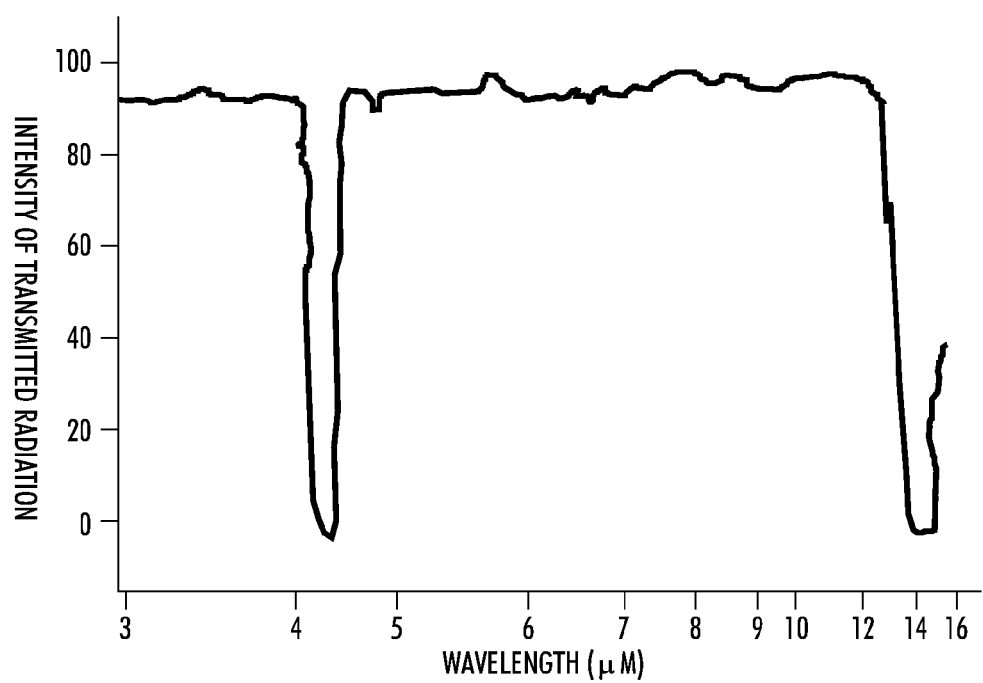
FIG. 5 shows the infrared spectrum of a gaseous sample of $CO_2$.

FIG. 5 shows another infrared spectrum of a sample of carbon dioxide. Note that the intensity of the transmitted light is close to 100% everywhere except where the sample absorbs: at 2349 $cm^{-1}$ (4.26 μm), and at 667 $cm^{-1}$ (15.00 μm).

Figure 6:
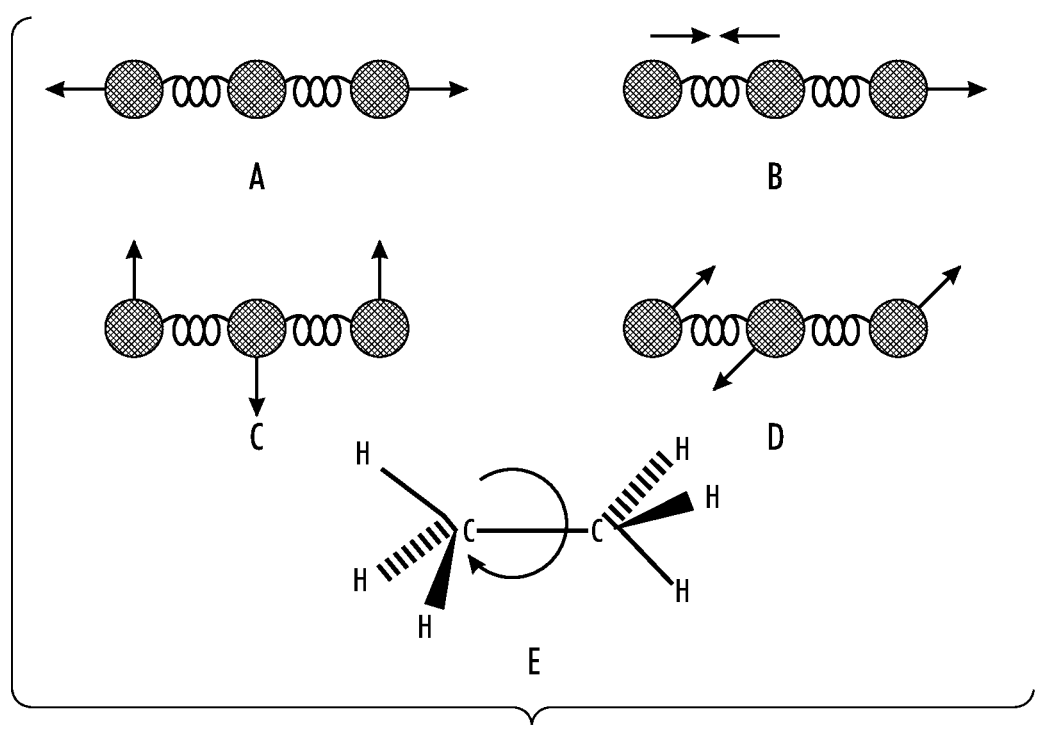
FIGS. 6A-E illustrates various vibrational modes of a molecule of $CO_2$ (6A-D), and the torsional mode of a molecule of ethane (6E).

Because $CO_2$ has more than two atoms, it can vibrate different ways. These different types of motion occur at different frequencies. The frequencies of these roto-vibrational motions may be calculated based upon the mass of the atoms involved and the strength of their bonds. $CO_2$ is a linear molecule and thus has (3×3)−5=4 vibrations. In FIG. 6, these vibrational modes are shown where the arrows indicate a direction of motion. Vibrations (6A) and (6B) represent the stretching of the bonds, one in a symmetric fashion (6A) in which both C═O bonds lengthen and contract together (in-phase), and the other in an asymmetric fashion (6B) in which one bond shortens while the other lengthens. The asymmetric stretch is infrared active because there is a change in the molecular dipole moment during vibration. To be "active" means that absorption of a photon to excite the vibration is allowed by the rules of quantum mechanics. The infrared selection rule states that, for a particular vibrational mode to be observed (active) in the infrared spectrum, the mode must involve a change in the dipole moment of the molecule. Infrared radiation at 2349 $cm^{-1}$ (4.26 μm) excites this particular vibration. The symmetric stretch is not infrared active and so this vibration is not observed in the infrared spectrum of $CO_2$. The two equal-energy bending vibrations in $CO_2$ (6C) and (6D) are identical except that one bending mode is in the plane of the drawing sheet and one extends out of the plane of the sheet. Infrared radiation at 667 $cm^{-1}$ (15.00 μm) excites these vibrations.

In addition to bond stretching and bond bending, rotational vibrations such as rocking and twisting occur between adjacent portions of the molecule. Torsions involve changes in dihedral angles. No bonds are stretched and no bond angles change but the spatial relationship between the atoms attached to each of two adjacent atoms is subject to change. The torsional mode for the molecule of ethane in illustrated by way of example in (6E). Essentially, the stronger the bond, the more energy is required to excite the stretching vibration. This is seen in organic compounds where stretches for triple bonds occur at higher frequencies than stretches for double bonds (C═C, C═N, C═O), which are in turn at higher frequencies than single bonds (C—C, C—N, C—H, O—H, or N—H). Generally, the heavier the atom, the lower the frequencies for vibrations that involve that atom.

Flow Diagram of One Example Embodiment

Figure 7:
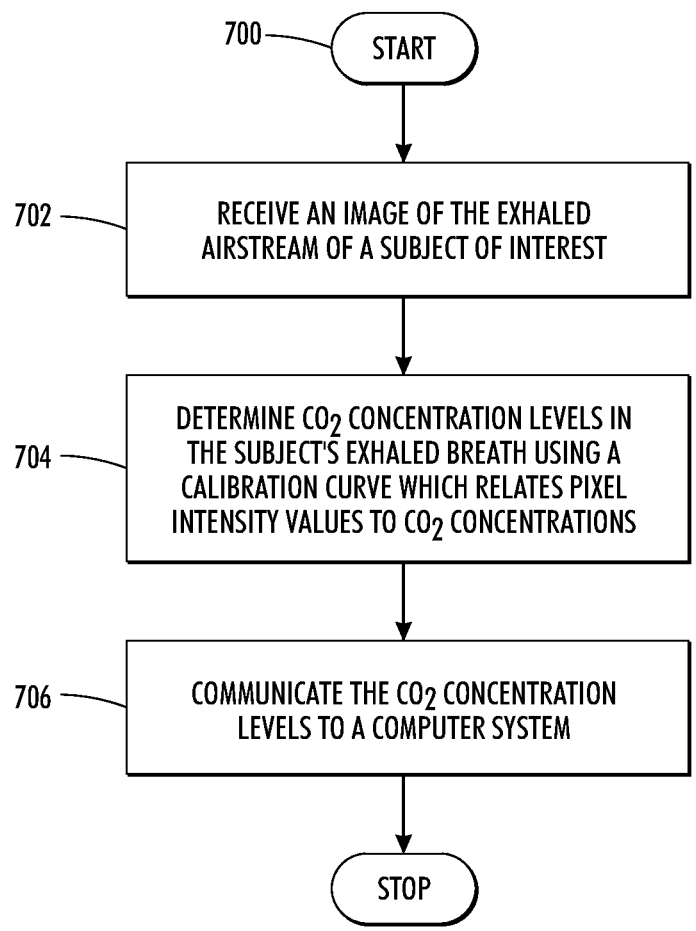
FIG. 7 is a flow diagram which illustrates one example embodiment of the present method for image-based determination of $CO_2$ concentration in exhaled breath.

Reference is now being made to the flow diagram of FIG. 7 which illustrates one example embodiment of the present method for image-based determination of carbon dioxide ($CO_2$) concentration in exhaled breath. Flow processing begins at step 700 and immediately proceeds to step 702.

At step 702, receive an IR image of the exhaled airstream of a subject of interest captured using a mid-wave infrared camera system having at least one optical filter tuned to the infrared absorption band of $CO_2$. As previously discussed, the camera system is designed to collect the emissivity of radiation caused by the vibrations of the atoms in the $CO_2$ molecule. One example IR image of a subject of interest is shown in FIG. 2. Each of the received images comprises, at least in part, an array of pixels having respective intensity values obtained at the absorption band of $CO_2$. The IR images are preprocessing to isolate a region containing the exhalation airstream and the intensity values of the pixels in this region are normalized by a value of a known radiance such that an identified region of the nose or face of the subject of interest (shown by way of example at 802 of FIG. 8). The captured images are processed on a frame-by-frame basis such that time series data is retained. In one embodiment of pre-processing, pixels are identified which locate a facial feature associated with respiration. From the location of the identified facial features, pixels in the area which defines the subject's exhalation airstream (803 of FIG. 8) can be isolated and processed. Histograms of pixel intensities in the identified exhalation airstream area are analyzed to select the region where the $CO_2$ emitted radiance is at a highest value. This maximum in pixel intensities corresponds to the center or core of the exhaled airstream where the concentrations of exhaled gases are highest. In frames where the inhalation process happens, the radiance of the $CO_2$ is equal to the radiance of the background because there is no exhalation airstream during inhalation. This is readily confirmed by an analysis of pixel intensity histograms observed on a frame-by-frame basis as the subject breathes in and out. The size and shape of the subject's facial features associated with respiration and the region of the exhalation plume can be fixed after conducting sensitivity analysis such that these regions can be readily isolated in the captured video sequence, extracted automatically through background and facial features detection, and the pixels processed accordingly. FIG. 8C plots time series data of the digital counts for the $CO_2$ exhalation (in that example, the mean value of nose is 193.42), as explained herein further in greater detail.

At step 704, determine $CO_2$ concentration levels in the exhaled airstream using a calibration curve which relates pixel intensity values to $CO_2$ concentrations. One example calibration curve is shown and discussed with respect to FIG. 1. The calibration curve is derived using a physics-based parameterized model which relates pixel intensity to $CO_2$ concentration in mmHg units. Alternatively, the calibration is derived by experimental methods. In the instance where a video stream of time sequential images has been received, a respiration rate is also determined for the subject of interest.

At step 706, communicate the $CO_2$ concentration levels to a computer system. In other embodiments, the $CO_2$ concentration levels are communicated to a memory, a storage device, a graphical display, a messaging system, a cellular device, or communicated to a remote device over a network for storage or further processing. Thereafter, in the embodiment of FIG. 7, further processing stops.

It should be appreciated that the flow diagrams hereof are illustrative. One or more of the operative steps illustrated in the flow diagram may be performed in a differing order. Other operations, for example, may be added, modified, enhanced, condensed, integrated, or consolidated with the steps thereof. Such variations are intended to fall within the scope of the appended claims. All or portions of the flow diagrams may be implemented partially or fully in hardware in conjunction with machine executable instructions.

$CO_2$ Concentration Determination

The radiance of $CO_2$ in the spectral window of observation depends on several factors: atmospheric pressure (P), temperature (T in degrees Kelvin), volume mixing ratio (vmr), and depth of the sample (L). Atmospheric pressure needs to be accounted for because molecular resonances are broadened by collisions with background molecules due to pressure. Atmospheric pressure is 1 bar (1013.25 mbars) at sea level. Temperature determines the amplitude of the molecular vibrations. The thermal energy drives the various molecular roto-vibrational modes (shown by way of example in FIG. 6) allowing them to fluoresce giving off a radiance which can be observed with a camera. The volume mixing ratio (vmr) is the fractional number of molecules of a species in a volume. In practice, the vmr is the percentage of gas of interest that can be converted into any other unit of partial volume such as ppm or mmHg just by multiplying by a corresponding factor. Individual vmrs and their sum must be between 0 and 1. If the vmr sums to less than 1, the rest of the gas in the cell is assumed to be optically transparent. Line shapes for molecules with a vmr less than 1 are air-broadened. An example depth of the sample (L) is shown at $L_2$ (914 of FIG. 9). The deeper the exhalation plume being detected, the more radiance it emits up to the limit where it saturates by self-absorption. For absolute measurements of $CO_2$ concentration, the depth needs to be measured with a high degree of accuracy.

Figure 9:
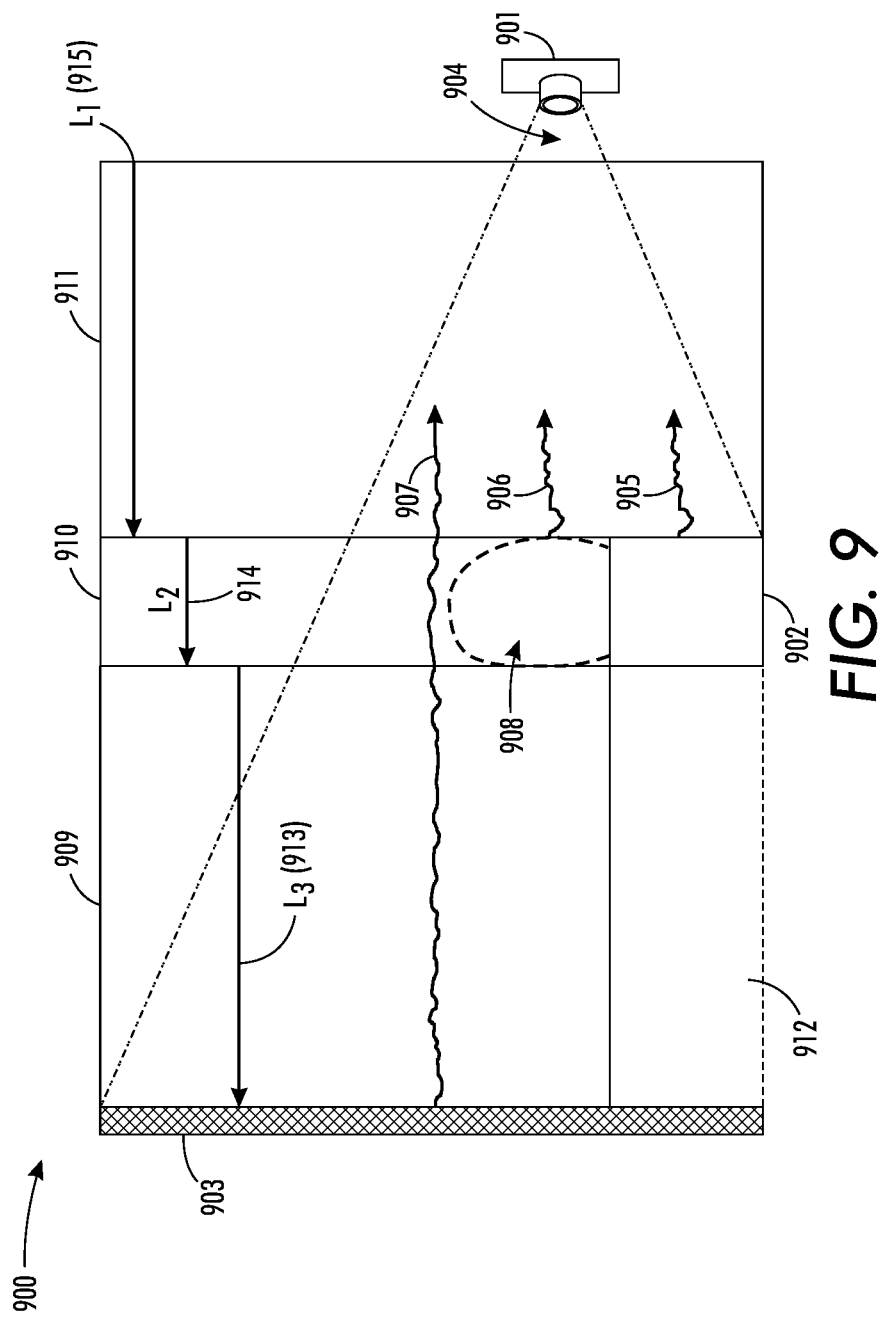
FIG. 9 illustrates different observable radiance paths detected by the camera.

Reference is now being made to FIG. 9 which illustrates different observable radiance paths detected by an IR camera 901 with a 4.2 to 4.4 μm band-pass filter. As the subject continues with their breathing cycle, different levels of intensity can be observed.

Room 900 has camera 901 positioned in such a manner as to capture an IR image of the profile of the face or nose of a subject 902 of interest (as shown in the image of FIG. 2). The subject is standing in front of a wall 903 in the camera's field of view 904. Radiances along radiance paths 905, 906, and 907, are from the subject's 902 nose/face, the exhalation airstream 908, and wall 903, respectively. It should be appreciated that the radiance paths are illustrative. Several different regions 909, 910, and 911, in room 900 can be generally identified. Region 912 is blocked by subject 902. Radiances $R_o$ along radiance path 905 are from the side of the subject's nose/face 902. The subject's nose has an emissivity ($e_{skin}$). The emissivity of skin is approximately the same for people of any skin type (≈0.97). The subject's nose has a temperature ($T_{nose}$) that gives a blackbody radiance $R_{BB}$, when corrected for the distance to the camera 915, the ambient $CO_2$ concentration, the ambient atmospheric pressure and ambient temperature. Radiances $R_{CO_2}$ along radiance path 906 are from the exhalation airstream plume 908. During inhalation when exhalation plume 908 is not present due to air being drawn into the lungs rather than being expelled out of the lungs, radiances $R^o$ along radiance path 907 are emitted from wall 903 and other background objects present. $R^o$ is a value already corrected for the distance 913, 915, 915 to the camera, the ambient $CO_2$ concentration, the ambient atmospheric pressure and ambient temperature. The wall has an emissivity ($e_{wall}$) and a temperature ($T_{wall}$). The digital intensities $I_o$, $I_{BB}$, and $I_{CO_2}$, are due to their respective radiances ($R_o$, $R_{BB}$, and $R_{CO_2}$), emitted by the objects they represent (plus image noise due to scattered light and other sources of camera noise). The temperature of the wall ($T_{wall}$) and the temperature of the nose ($T_{nose}$) can be measured by a thermometry function of the same camera used for $CO_2$ measurements. Since the digital intensities on the images are not calibrated for radiance, a known radiance is used as a reference to calibrate the camera digital intensities to localized radiances. One reference for calibration is temperature of the subject's nose because the temperature of the nose is an approximately constant temperature (34° C.+/−3° C.) having a narrow temperature range when expressed in Kelvin (307° K+/−3° K).

Radiances can be readily calculated using molecular spectral information obtained from the High-Resolution Transmission Molecular Absorption Database (HITRAN) which is maintained by the Atomic and Molecular Physics Division of the Harvard-Smithsonian Center for Astrophysics. HITRAN is a compilation of spectroscopic parameters that a variety of computer codes use to predict and simulate the transmission and emission of light in the atmosphere. The database is downloadable from Harvard's website [http://www.cfa.harvard.edu/hitran/]. The HITRAN database can be processed using a custom-made computer code or a commercial software such as "Spectral Calc" which simulates particular conditions such as temperature, pressure, volume mixing ratio, and volume depths/distances. Spectral Calc website [http://spectralcalc.com] also provides some spectroscopy and remote sensing tools for researchers, teachers and students. $CO_2$ concentrations are determined using a transfer function that converts intensities ($I_{CO_2}$) measured from emissions detected in the subject's exhalation plume into calculated $CO_2$ radiances.

Figure 10:
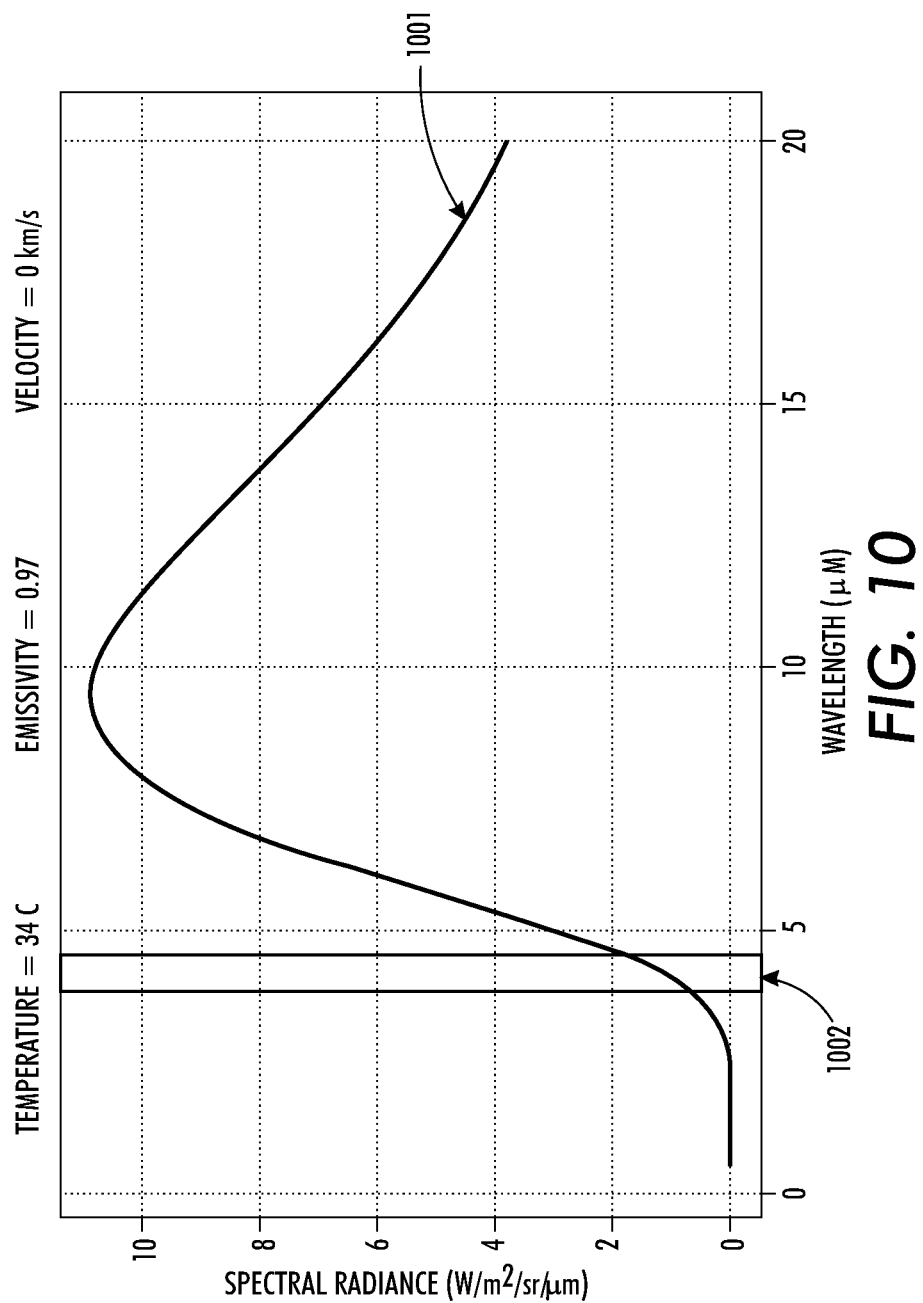
FIG. 10 shows the blackbody radiance due to a nose or face at 34° C.

FIG. 10 shows the blackbody radiance 1001 emitted from the skin of the nose or face at 34° C. Region 1002 defines a spectral region that is transmitted by the band-pass filter to the camera. The wall behind the subject has a similar blackbody radiation pattern. Assuming that a level of noise N is common to each of the regions 909, 910, and 911 (of FIG. 9), then the relationship between the intensities and the calculated/actual radiances can be represented by the following:

$$I_o = \alpha(R_o + N) \quad (1)$$

$$I_{BB} = \alpha(R_{BB} + N) \quad (2)$$

$$I_{CO_2} = \alpha(R_{CO_2} + N) \quad (3)$$

where $\alpha$ is the gain of the camera. The unknowns are $\alpha$, N, and $R_{CO_2}$.

Computing $CO_2$ Concentrations

Knowledge of the intensity on the camera $I_{CO_2}$ corresponding to the exhaled $CO_2$ region, allows us to compute the breath $CO_2$ concentration $R_{CO_2}$. $R_{CO_2}$ can be determined by solving Eqs. (1) through (3) for $R_{CO_2}$, which produces the following:

$$R_{CO_2} = \frac{R_{BB}(I_{CO_2} - I_o) + R_o(I_{BB} - I_{CO_2})}{(I_{BB} - I_o)} \quad (4)$$

$R_o$ and $R_{BB}$ are calculated from known parameters using the HITRAN database.

$$R_o = R_o(T_{wall}, e_{wall}, L_1, L_2, T_{room}, L_3, P, VMR_{CO_2\text{-}room}) \quad (5)$$

$$R_{BB} = R_{BB}(T_{nose}, e_{nose}, T_{room}, L_3, P, VMR_{CO_2\text{-}room}) \quad (6)$$

where the parameters above are known without knowledge of the concentrations of the breath $CO_2$ level, and $R_{CO_2}$ is used to determine the breath $CO_2$ concentration ($VMR_{CO_2\text{-}breath}$) via a transfer function given by:

$$R_{CO_2} = R_{CO_2}(T_{wall}, e_{wall}, L_1, T_{room}, L_2, L_3, P, VMR_{CO_2\text{-}breath}) \quad (7)$$

where $VMR_{CO_2\text{-}breath}$ is unknown, and $R_{CO_2}$ is a function of the known parameters listed inside of the parenthesis of equation (7) and of $VMR_{CO_2\text{-}breath}$.

Eq. (7) gives a transfer function that relates $R_{CO_2}$ to $VMR_{CO_2\text{-}breath}$ that can be written in mmHg (or in terms of a percentage).

Figure 11:
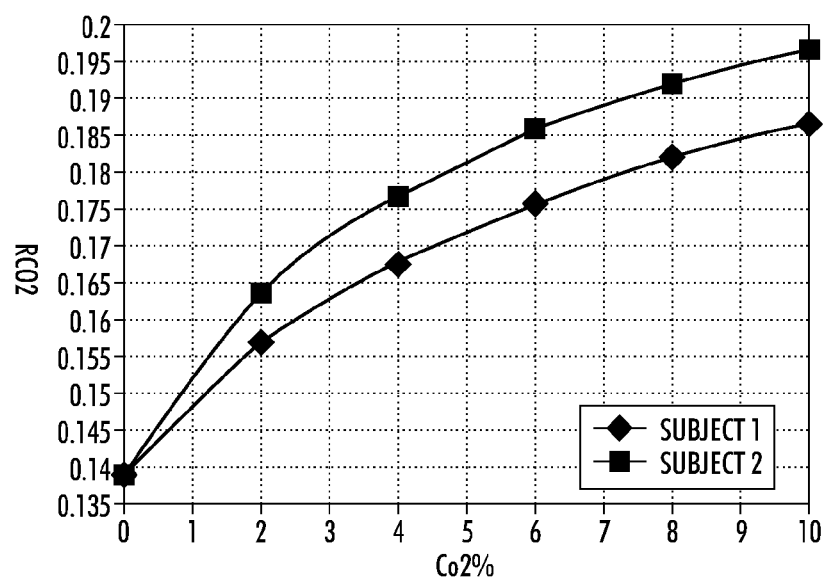
FIG. 11 shows two transfer functions plotted according to the data of the Table.

FIG. 11 plots the transfer functions for subjects 1 and 2 according to the parameters of the associated Table. The transfer function for subjects 1 and 2 are different because the distances, temperatures, and various dimensions involved in the measurements were different. For example, subject 2 was breathing through the mouth (4 cm) while subject 1 was breathing through the nose (3 cm). Distances to the camera and to the wall were also different. The data of FIG. 11 can be converted to mmHg to create a transfer function.

Figure 8A:
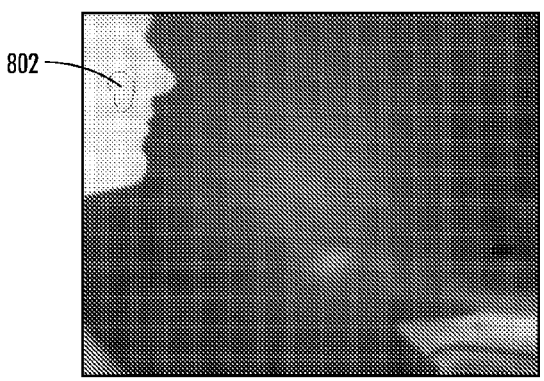
FIGS. 8A-C illustrates a facial region (8A), a region containing the exhalation plume (8B), and time series data (8C) of the digital counts for the $CO_2$ region of interest.
Figure 8B:
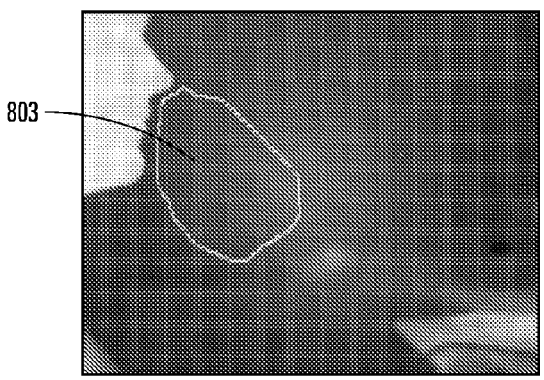
Figure 8C:
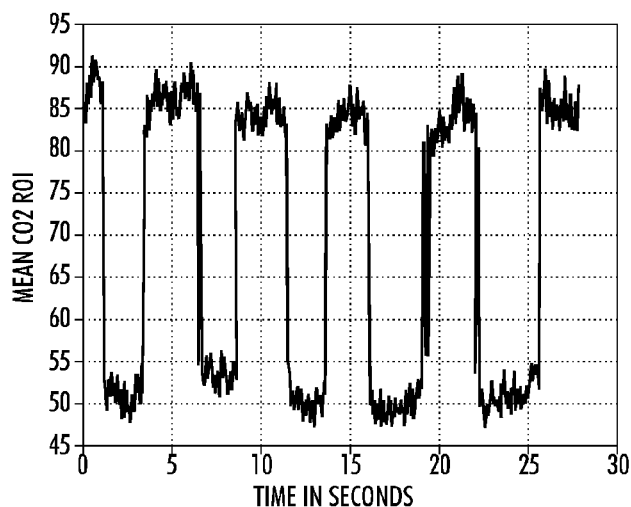
Figure 12:
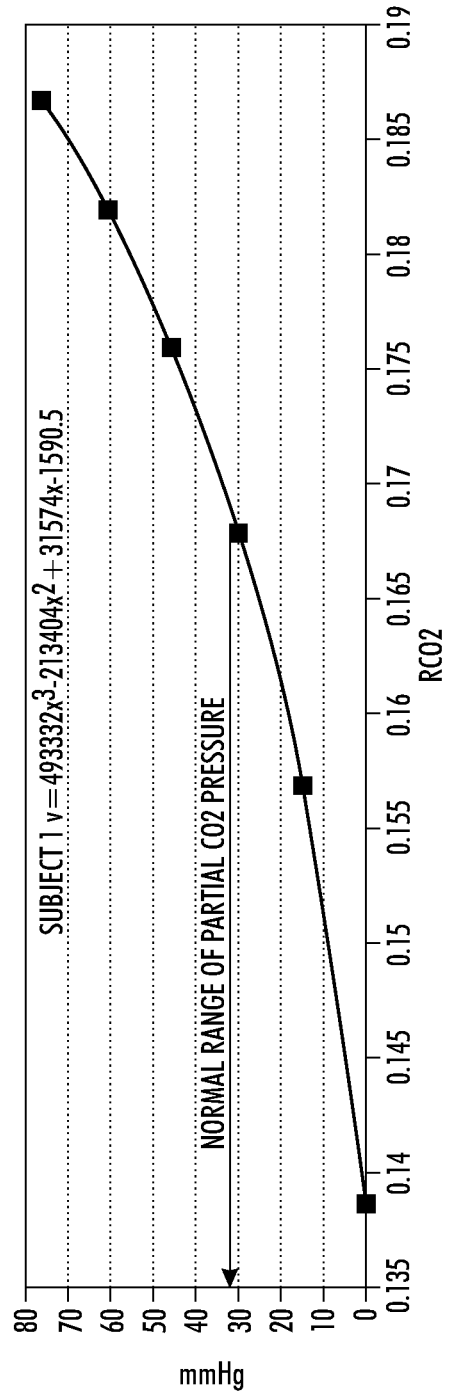
FIG. 12 shows the transfer function for subject 1 to convert $R_{CO_2}$ into mmHg.

FIG. 12 plots the transfer function for subject 1 to convert $R_{CO_2}$ into mmHg. $R_{CO_2}$ is the radiance of the $CO_2$ exhaled gas calculated using information from the digital image and from known parameters. For subject 1, for example, the pre-processed digital counts were extracted from FIG. 8C where, for one of the point is the chart, $$I_o = 50 \text{ and } I_{CO_2} = 84, \quad (8)$$

and from identified region 802 of FIG. 8A, we obtain the intensity $$I_{BB} = 193.42. \quad (9)$$

The parameters in this example are accordingly to the Table of FIG. 11. It should be appreciated that these values can be accurately measure by other means.

Using a spectroscopic model (such as Spectra Calc) with the inputs of the Table of FIG. 11, the following can be readily determined:

$$R_o = 0.13894 \frac{W}{m^2}/sr \quad (10)$$

$$R_{BB} = 0.267 \frac{W}{m^2}/sr \quad (11)$$

Inputting the values of Eqs. (8), (9), (10) and (11) into Eq. (4), produces:

$$R_{CO_2} = 0.1695 \frac{W}{m^2}/sr. \quad (12)$$

The value of $R_{CO_2}$ (derived in Eq. (12)) is used in the transfer function (created in FIG. 11) to determine the percentage of $CO_2$ in the exhaled breath in mmHg, i.e., 32.56 mmHg using those values.

Figure 13A:
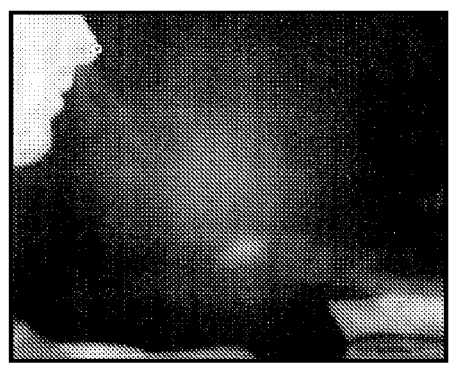
FIGS. 13A-C show a first subject (13A), a $CO_2$ partial pressure in exhaled air (13B) calculated for the conditions of measurement of the first subject, and the power spectrum (13C) of the time series data of 13B.
Figure 13B:
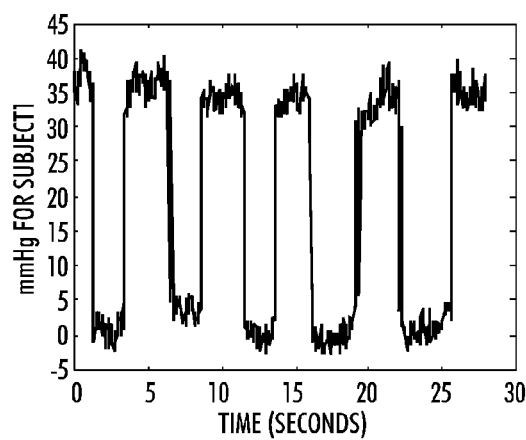

FIG. 13B plots $CO_2$ levels after applying the transfer function of FIG. 11A on the Y axis of FIG. 8C.

Respiration Rate Determination

Figure 13C:
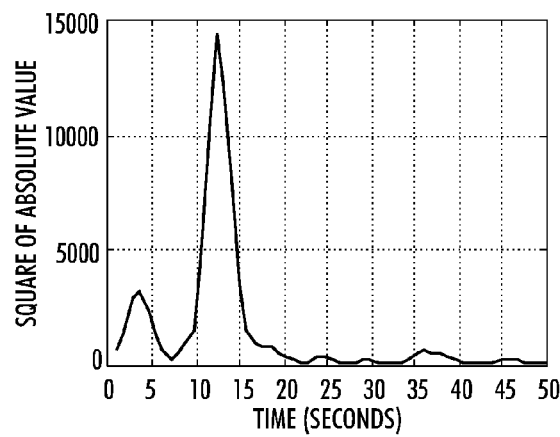
Figure 14A:
FIGS. 14A-C show a second subject (14A), a $CO_2$ partial pressure in exhaled air (15B) calculated for the conditions of measurement of the second subject, and the power spectrum (14C) of the time series data of 14B.
Figure 14B:
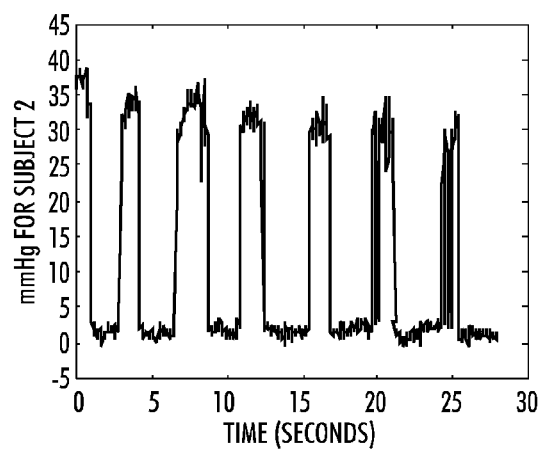
Figure 14C:
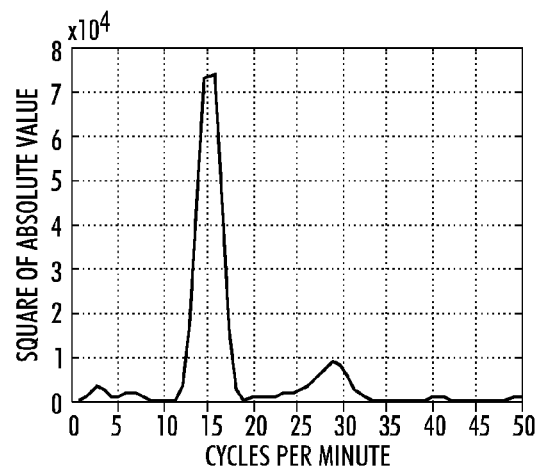

A Fast Fourier Transform (FFT) based method can be used to estimate human breathing rate using RR time-series data. The power spectrum of the time series data shows a dominant frequency. In FIG. 13, a first subject (13A) has a $CO_2$ partial pressure in exhaled air calculated (13B) for the conditions of measurement of the first subject, using same data shown in FIG. 8. FIG. 13C shows the power spectrum of the time series data of 13B (dominant frequency: 12.3 cpm). In FIG. 14, a second subject (14A) has a $CO_2$ partial pressure in exhaled air calculated (14B) for the conditions of measurement of the second subject. FIG. 14C shows the power spectrum of the time series data of (14B), (dominant frequency: 15.5 cpm). Table A below shows results.

TABLE A

| | Respiration Rate (breaths per minute) | End Tidal$CO_2$ (partial pressure in exhaled air)* |
| --- | --- | --- |
| Subject 1 (nose) | 12.3 bpm | (34 ± 5) mmHg |
| Subject 2 (mouth) | 15.5 bpm | (40 ± 5) mmHg |

(*Atmospheric pressure in 760 mmHg)

Figure 15:
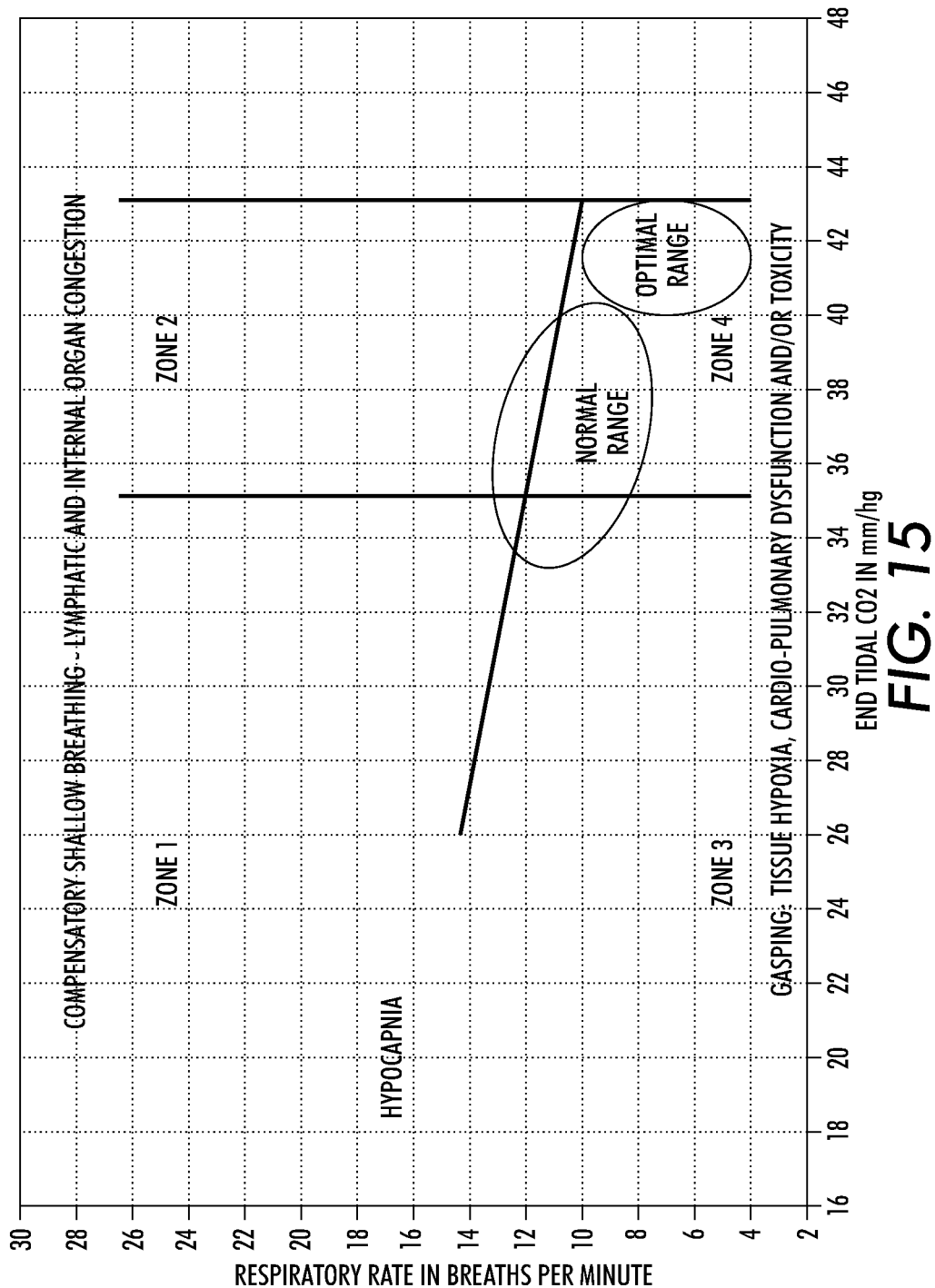
FIG. 15 plots $CO_2$ levels in exhaled air (X-axis) against respiratory rate (Y-axis)

The results of TABLE A can be compared to literature data shown in FIG. 15. In FIG. 15, $CO_2$ levels in exhaled air (X-axis) are plotted against respiratory rate (Y-axis). An examination of FIG. 15 shows that the values obtained (i.e., 32.56 mmHg) are compatible with a normal range.

Example Image Processing System

Figure 16:
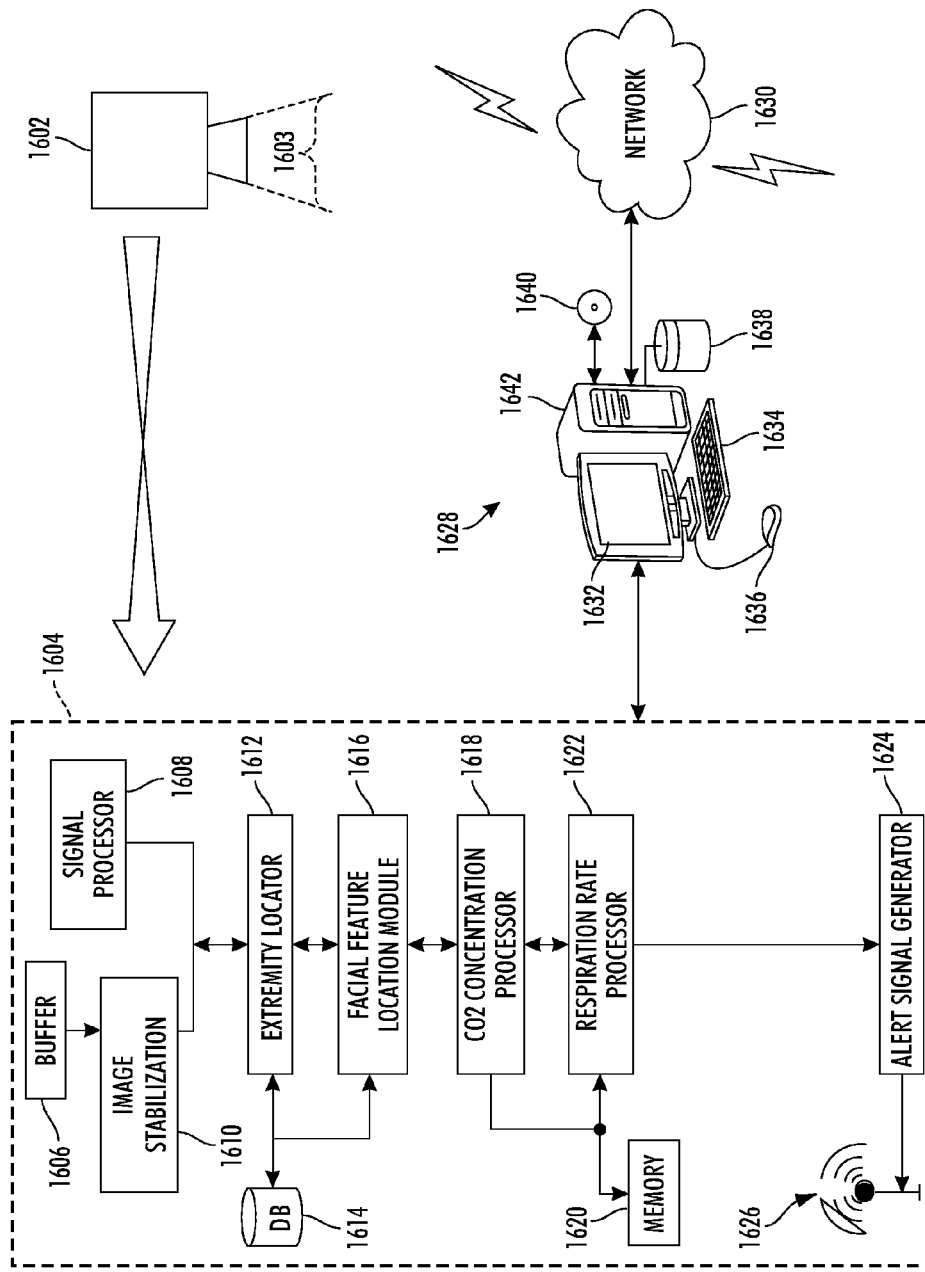
FIG. 16 is a block diagram of an example networked respiration monitoring system capable of implementing various aspects of the present method as described with respect to the flow diagram of FIG. 7.

Reference is now being made to FIG. 16 which is a block diagram of one example respiration monitoring system for implementing various aspects of the present method as described with respect to the flow diagram of FIG. 7.

In FIG. 16, mid-wave infrared camera 1602 captures one or more IR images of a subject of interest whose head and face are in the camera's field of view 1603. The captured images are communicated to image processing system 1604 shown comprising a Buffer 1606 for queuing the received images for processing. Buffer 1606 may further store data and mathematical formulas and representations as necessary to process the images according to various embodiments hereof. Signal Processor 1608 receives the image signals from camera 1602 and processes the pixel intensity values to ensure that these values are within a predefined range and to associate pixels intensities with image areas within a given image frame. Image Stabilizer 1610 is provided for those systems where noise in the video sequence from either the motion of the camera or movement of the subject needs to be compensated for using, for example, image segmentation and point feature tracking. Such techniques are well known in the image processing arts. The processed image data are provided to Extremity Locator 1612 which identifies extremities of the subject's head and face. Facial Feature Location Module 1616 receives the identified head and face extremities from Extremity Locator Module 1612 and locational relationships are retrieved from database 1614 and used to determine a location of the subject's facial features associated with respiration such as their nose and mouth. CO2 Concentration Module 1618 determines the $CO_2$ concentration of the subject's exhaled breath in accordance with the teachings hereof. Respiration Rate Processor 1622 determines the subject's respiration rate in accordance with the teachings hereof. Values generated are stored to Memory 1620. Alert Signal Generator 1624 outputs a signal 1626 if either the respiration rate or the determined $CO_2$ concentration falls outside pre-defined threshold levels.

Various portions of the IR images captured by mid-wave infrared camera 1602 may be stored to Memory 1620 and/or to Storage Device 1614 or may be communicated to Workstation 1628 for storage or processing. It should be appreciated that some or all of the functionality performed by any of the modules or processing units of system 1604 can be performed, in whole or in part, by workstation 1628. Workstation 1628 is in communication with network 1630 via a communications interface (not shown). Workstation 1628 is shown comprising a display monitor 1632 for displaying information and for effectuating a user input or selection. Display 1632 may be placed in communication with image processor system 1604 and/or camera system 1602 such that images obtained thereby can be viewed on the monitor display. A user or technician of the system of FIG. 16 may use the graphical user interface of workstation 1628, e.g., keyboard 1634 and mouse 1636, to identify regions of interest, set parameters, select pixels, frames, images, and/or regions of images for processing. These may be stored and/or retrieved from storage medium 1638 or to computer readable media 1640. Information stored to media 1640 can be retrieved by a media reader such as, for example, a CD-ROM drive, located inside of computer case 1642. Any of the modules and processing units of FIG. 16 can be placed in communication with database 1638 and may store/retrieve therefrom data, variables, records, parameters, functions, machine readable/executable program instructions required to perform their intended functions. Moreover each of the modules of system 1604 may be placed in communication with one or more devices over network 1630.

It should also be appreciated that various modules may designate one or more components which may, in turn, comprise software and/or hardware designed to perform the intended function. A plurality of modules may collectively perform a single function. Each module may have a specialized processor capable of executing machine readable program instructions. A module may comprise a single piece of hardware such as an ASIC, electronic circuit, or special purpose processor. A plurality of modules may be executed by either a single special purpose computer system or a plurality of special purpose computer systems operating in parallel. Connections between modules include both physical and logical connections. Modules may further include one or more software/hardware modules which may further comprise an operating system, drivers, device controllers, and other apparatuses some or all of which may be connected via a network.

It is also contemplated that one or more aspects of the present method may be implemented on a dedicated computer system and may also be practiced in distributed computing environments where tasks are performed by remote devices that are linked through a network. The teachings hereof can be implemented in hardware or software using any known or later developed systems, structures, devices, and/or software by those skilled in the applicable art without undue experimentation from the functional description provided herein with a general knowledge of the relevant arts.

One or more aspects of the methods described herein are intended to be incorporated in an article of manufacture, including one or more computer program products, having computer usable or machine readable media. For purposes hereof, a computer usable or machine readable media is, for example, a floppy disk, a hard-drive, memory, CD-ROM, DVD, tape, cassette, or other digital or analog media, or the like, which is capable of having embodied thereon a computer readable program, one or more logical instructions, or other machine executable codes or commands that implement and facilitate the function, capability, and methodologies described herein. Furthermore, the article of manufacture may be included on at least one storage media readable by a machine architecture or image processing system embodying executable program instructions capable of performing the methodology described in the flow diagrams. The article of manufacture may be included as part of an operating system, a plug-in, or may be shipped, sold, leased, or otherwise provided separately, either alone or as part of an add-on, update, upgrade, or product suite.

It will be appreciated that various of the above-disclosed and other features and functions, or alternatives thereof, may be desirably combined into many other different systems or applications. Various presently unforeseen or unanticipated alternatives, modifications, variations, or improvements therein may become apparent and/or subsequently made by those skilled in the art, which are also intended to be encompassed by the following claims. Accordingly, the embodiments set forth above are considered to be illustrative and not limiting. Various changes to the above-described embodiments may be made without departing from the spirit and scope of the invention. The teachings of any printed publications including patents and patent applications, are each separately hereby incorporated by reference in their entirety.

What is claimed is:

1. A method for image-based determination of carbon dioxide ($CO_2$) concentration in exhaled breath in a non-contact, minimally invasive, respiration measurement environment, the method comprising:
  receiving at least one IR image of the exhaled airstream of a subject of interest, said image having been captured using a mid-wave infrared camera system having at least one optical filter tuned to an infrared absorption band of $CO_2$, each of said received images comprising, in part, an array of pixels having respective measured intensity values obtained at an absorption band of $CO_2$;

processing, via a processor, said IR image to isolate pixels in regions associated with background objects in said image, an area of said subject's nose and face, and said exhaled airstream; and to obtain a digital intensity value for each region comprising values of $I_O$, $I_{BB}$ and $I_{CO_2}$, respectively, where $I_O$ is the intensity value in said area of said subject's nose and face, $I_{BB}$ is the intensity value in said background, and $I_{CO_2}$ is the intensity value of said exhaled airstream;

determining respective radiances $R_{BB}$ and $R_O$ from each of said digital intensity values $I_{BB}$ and $I_O$, where $R_{BB}$ is a background radiance and, $R_O$ is a radiance of said nose and face;

determining a radiance of said subject's exhaled airstream, $R_{CO_2}$, based upon said radiances $R_{BB}$ and $R_O$ and said digital intensities $I_O$, $I_{BB}$ and $I_{CO_2}$; and determining $CO_2$ concentration level of said subject's exhaled airstream based on said determined radiance $R_{CO_2}$.

2. The method of claim 1, wherein said camera system is designed to collect the light emitted by the roto-vibrational radiation from $CO_2$ molecules, said system including an infrared camera with a sensitivity band that includes 4.0-4.5 um and a spectral band-pass filter which allows $CO_2$ emission light to enter a lens of said camera.

3. The method of claim 1, wherein said optical filter comprises a narrow band-pass filter which increases a contrast of $CO_2$ relative to background radiation.

4. The method of claim 1, further comprising, in the instance wherein a video stream of time sequential images has been received, determining a respiration rate for said subject of interest based upon a mathematical analysis of time-dynamics of an inhalation-exhalation pattern of said subject.

5. The method of claim 4, further comprising using said $CO_2$ concentration levels and said respiration rate to determine whether said subject of interest is in a state of any of: hyperventilation and hypoventilation.

6. The method of claim 1, further comprising communicating said $CO_2$ concentration levels to any of: a memory, a storage device, a graphical display, a telephonic messaging system, and a computer workstation.

7. The method of claim 1, wherein said radiance $R_{CO_2}$ comprises:

$$R_{CO_2} = \frac{R_{BB}(I_{CO_2} - I_o) + R_o(I_{BB} - I_{CO_2})}{(I_{BB} - I_o)}.$$

8. A system for image-based determination of carbon dioxide ($CO_2$) concentration in exhaled breath, the system comprising:

a processor in communication with a camera system, said processor configured to execute machine readable instructions for performing the method of:

receiving at least one IR image of the exhaled airstream of a subject of interest, said image having been captured using a mid-wave infrared camera system having at least one optical filter tuned to an infrared absorption band of $CO_2$, each of said received images comprising, in part, an array of pixels having respective measured intensity values obtained at an absorption band of $CO_2$;

processing said IR image to isolate pixels in regions associated with background objects in said image, an area of said subject's nose and face, and said exhaled airstream; and to obtain a digital intensity value for each region comprising values of $I_O$, $I_{BB}$ and $I_{CO_2}$, respectively, where $I_O$ is the intensity value in said area of said subject's nose and face, $I_{BB}$ is the intensity value in said background, and $I_{CO_2}$ is the intensity value of said exhaled airstream;

determining respective radiances $R_{BB}$ and $R_O$ from each of said digital intensity values $I_{BB}$ and $I_O$, where $R_{BB}$ is a background radiance and, $R_O$ is a radiance of said nose and face;

determining a radiance of said subject's exhaled airstream, $R_{CO_2}$, based upon said radiances $R_{BB}$ and $R_O$ and said digital intensities $I_O$, $I_{BB}$ and $I_{CO_2}$; and determining $CO_2$ concentration level of said subject's exhaled airstream based on said determined radiance $R_{CO_2}$.

9. The system of claim 8, wherein said camera system is designed to collect the light emitted by the roto-vibrational radiation from $CO_2$ molecules, said system including an infrared camera with a sensitivity band that includes 4.0-4.5 um and a spectral band-pass filter which allows $CO_2$ emission light to enter a lens of said camera.

10. The system of claim 8, wherein said optical filter comprises a narrow band-pass filter which increases a contrast of $CO_2$ relative to background radiation.

11. The system of claim 8, further comprising, in the instance wherein a video stream of time sequential images has been received, determining a respiration rate for said subject of interest based upon a mathematical analysis of time-dynamics of an inhalation-exhalation pattern of said subject.

12. The system of claim 11, further comprising using said $CO_2$ concentration levels and said respiration rate to determine whether said subject of interest is in a state of any of: hyperventilation and hypoventilation.

13. The system of claim 8, further comprising communicating said $CO_2$ concentration levels to any of: a memory, a storage device, a graphical display, a telephonic messaging system, and a computer workstation.

14. The system of claim 8, wherein said radiance $R_{CO_2}$ comprises:

$$R_{CO_2} = \frac{R_{BB}(I_{CO_2} - I_o) + R_o(I_{BB} - I_{CO_2})}{(I_{BB} - I_o)}.$$

15. A non-transitory computer useable medium having a computer readable program for image-based determination of carbon dioxide ($CO_2$) concentration in exhaled breath in a non-contact, minimally invasive, respiration measurement environment embodied thereon that, when executed on a computer, causes the computer to perform a method comprising:

receiving at least one IR image of the exhaled airstream of a subject of interest, said image having been captured using a mid-wave infrared camera system having at least one optical filter tuned to an infrared absorption band of $CO_2$, each of said received images comprising, in part, an array of pixels having respective measured intensity values obtained at an absorption band of $CO_2$;

processing said IR image to isolate pixels in regions associated with background objects in said image, an area of said subject's nose and face, and said exhaled airstream; and to obtain a digital intensity value for each region comprising values of $I_O$, $I_{BB}$ and $I_{CO_2}$, respectively, where $I_O$ is the intensity value in said area of said subject's nose and face, $I_{BB}$ is the intensity value in said background, and $I_{CO_2}$ is the intensity value of said exhaled airstream;

determining respective radiances $R_{BB}$ and $R_O$ from each of said digital intensity values $I_{BB}$ and $I_O$, where $R_{BB}$ is a background radiance and, $R_O$ is a radiance of said nose and face;

determining a radiance of said subject's exhaled airstream, $R_{CO_2}$, based upon said radiances $R_{BB}$ and $R_O$ and said digital intensities $I_O$, $I_{BB}$ and $I_{CO_2}$; and determining $CO_2$ concentration level of said subject's exhaled airstream based on said determined radiance $R_{CO_2}$.

16. The non-transitory computer useable medium of claim 15, wherein said camera system is designed to collect the light emitted by the roto-vibrational radiation from $CO_2$ molecules, said system including an infrared camera with a sensitivity band that includes 4.0-4.5 μm and a spectral band-pass filter which allows only $CO_2$ emission light to enter a lens of said camera.

17. The non-transitory computer useable medium of claim 15, wherein said optical filter comprises a narrow band-pass filter which increases a contrast of $CO_2$ relative to a background radiation.

18. The non-transitory computer useable medium of claim 15, further comprising, in the instance wherein a video stream of time sequential images has been received, determining a respiration rate for said subject of interest based upon a mathematical analysis of time-dynamics of an inhalation-exhalation pattern of said subject.

19. The non-transitory computer useable medium of claim 18, further comprising using said $CO_2$ concentration levels and said respiration rate to determine whether said subject of interest is in a state of any of: hyperventilation and hypoventilation.

20. The non-transitory computer useable medium of claim 15, further comprising communicating said $CO_2$ concentration levels to any of: a memory, a storage device, a graphical display, a telephonic messaging system, and a computer workstation.

21. The non-transitory computer useable medium of claim 15, wherein said radiance $R_{CO_2}$ comprises:

$$R_{CO_2} = \frac{R_{BB}(I_{CO_2} - I_O) + R_O(I_{BB} - I_{CO_2})}{(I_{BB} - I_O)}$$

* * * * *